United States Patent [19]

Bombardelli et al.

[11] Patent Number: 5,525,609

[45] Date of Patent: Jun. 11, 1996

[54] **ALKALOIDS FROM *MAPPIA FOETIDA*, THE USE THEREOF AND FORMULATIONS CONTAINING THEM**

[75] Inventors: Ezio Bombardelli; Giuseppe Mustich; Luisella Verotta, all of Milan, Italy

[73] Assignee: Indena S.p.A., Milan, Italy

[21] Appl. No.: 273,510

[22] Filed: Jul. 11, 1994

[30] Foreign Application Priority Data

May 30, 1994 [IT] Italy ................................. MI94A1112

[51] Int. Cl.⁶ .............................................. C07D 491/22
[52] U.S. Cl. .................. 514/285; 546/48; 546/70
[58] Field of Search ................ 546/48, 70; 514/285

[56] References Cited

U.S. PATENT DOCUMENTS

| | | | |
|---|---|---|---|
| 5,264,591 | 11/1993 | Bombardelli et al. | 549/511 |
| 5,352,789 | 10/1994 | Hinz | 546/70 |

FOREIGN PATENT DOCUMENTS

| | | | |
|---|---|---|---|
| 00061482 | 3/1989 | Japan | 546/48 |

OTHER PUBLICATIONS

Wall et al. J. Am. Chem Soc vol. 88, pp. 3888–3891 (1966).

Wall et al. J. Med Chem vol. 29 pp. 1553–1555 (1986.

Gunasekera et al Jour. Nat. Prod (Lloydia) vol. 42 pp. 475–477 (1979.

*Primary Examiner*—Donald G. Daus
*Attorney, Agent, or Firm*—Bucknam and Archer

[57] ABSTRACT

The present invention relates to novel alkaloids from *Mappia foetida*, foetidine 1 and 2, having anticancer and antiviral properties. These alkaloids, soluble in water, are present in all the parts of the plant, and are the precursors of camptothecin and of 9-methoxy-camptothecin, which are alkaloids known to have pharmacodynamic properties but also to be insoluble in water. The particular water solubility of the novel compounds make them particularly suitable for the treatment of the patients by the parenteral route, avoiding the use of toxic excipients or of unsuitable chemical derivatizations.

5 Claims, No Drawings

ALKALOIDS FROM *MAPPIA FOETIDA*, THE USE THEREOF AND FORMULATIONS CONTAINING THEM

The present invention relates to novel alkaloids from *Mappia foetida*, the therapeutical use thereof and formulations containing them.

The alkaloids of the present invention have the following formula (I):

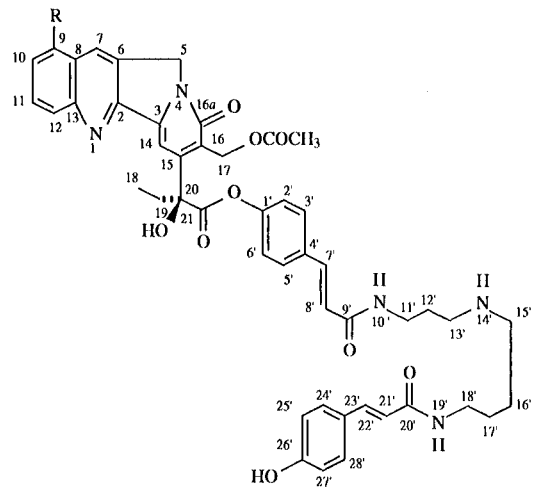

foetidine 1: R=H
foetidine 2: R=OCH$_3$.

By treatment with acids or bases, or with hydrolytic enzymes, foetidines 1 e 2 quantitatively release respectively: either the known alkaloid camptothecin, a molecule that has been widely tested pharmacologically and clinically, as such or in form of derivatives, in the oncology field and in the treatment of some viral diseases, or the 9-methoxy camptothecin, useful for the same indications.

Camptothecin, of formula (II)

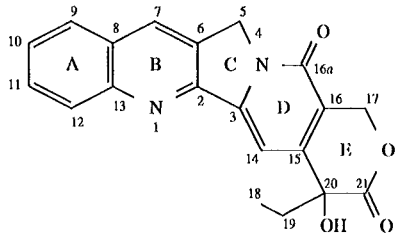

was first isolated, together with other compounds, from *Camptoteca acuminata* (Nyssaceae) and from other plants, among which *Mappia foetida* (Olinaceae); even though the latter has been studied for a long time, a further chemical screening surprisingly found novel alkaloids which give rise to camptothecin even in the processing of the plant raw extracts.

Particularly important among the compounds giving rise to camptothecin is foetidine 1, due to its relative abundance in the plant. The structural elucidation thereof, by spectroscopic analysis and chemical degradation, lead to the identification of a compound characterized in having a spermidine unit double esterified with coumaric acid, which is in its turn esterified with the open camptothecin unit (see Formula I). This compound is contained in all the parts of the plant, but particularly in the seeds and in the root, in amounts ranging from 0.1 to 0.5%. Compared with camptothecin, it has the advantage of being easily soluble in water at a slightly acid pH; on the contrary, camptothecin is completely insoluble in water and in all the biologically acceptable carriers, so that intensive efforts by the semi-synthetic point of view were carried out to obviate such a drawback.

Foetidine 1 is obtained extracting the various parts of the plant with low molecular weight aliphatic alcohols or ketones, alone or in admixture with water at room temperature; the extracts are concentrated at low temperature, preferably below 25° C. and under vacuum; the organic solvent is removed and the aqueous concentrate is extracted with chlorinated solvents to extract the poorly basic alkaloids, among which camptothecin, 9-methoxycamptothecin and mappicines; subsequently the aqueous phase is extracted with n-butanol or with water-immiscible alcohols which are then concentrated to dryness at low temperature under vacuum. The residue from the butanol extracts is purified on silica gel or similar adsorbents, using as eluents mixtures of chlorinated solvents, preferably methylene chloride, and aliphatic alcohols, preferably methanol or ethanol. Mixtures from 4:1 to 1:1 are preferably used. The fractions containing the alkaloids of the invention are combined, concentrated to dryness and the residue is further purified by preparative HPLC using, for example, a LiChroprep RP8 column and eluting with a methanol/water gradient, starting from a 1:1 methanol/water ratio until pure methanol. The alkaloid-containing fractions are concentrated at low temperature under vacuum and the aqueous concentrate is freeze-dried. The pure alkaloids are obtained by crystallization.

The resulting compounds were subjected to biological evaluation on human tumour cell lines (ovary, breast, colon, lung, resistant or not to other antitumourals, and the like) and on some virus strains. In fact, camptothecin, or better some of its derivatives, are known to have cytotoxic activity connected with the inhibition of DNA topoisomerases I and II.

The cytotoxicity, for example on a colon carcinoma cell line, is about 25 nM. The antiviral activity of foetidine 1, even though related to the different resistance of the strains, takes place at concentrations ranging from 1 to 100 ng/ml. Foetidine 2, which differs from foetidine 1 for a methoxyl at the 9-position, acts analogously. The herpes, cytomegalovirus and HIV viruses proved to be sensitive to the alkaloids of the invention.

The compounds of the invention can be incorporated in all kinds of pharmaceutical formulations, but above all they can easily be administered by the parenteral route in aqueous solutions at a pH compatible with blood, without causing problems such as precipitation or incompatibility. In the formulations, all the conventional pharmaceutical excipients can be used. The dosages of these novel alkaloids can range from 0.5 mg to 200 mg per dose and therapeutical cycle. Doses of about 50 mgs proved to be preliminarily effective.

The examples hereinbelow further illustrate the invention without limiting the scope thereof.

EXAMPLE 1

Preparation of foetidine 1 from *Mappia foetida* seeds.

5 kg of finely ground *Mappia foetida* seeds are extracted with 50 l of acetone for three times, under stirring at room temperature; the combined acetone extracts are concentrated under vacuum to 10 l; the concentrate is diluted with 10 l of a 1% citric acid solution; the insoluble materials are filtered and discarded, whereas the hydroacetone phase is counter-extracted with methylene chloride to exhaustion in the alkaloid extractable substances (camptothecin, methoxy-camptothecin etc.); the hydroacetone phase is concentrated to water and the concentrate is extracted, after neutralization at pH 7.5, with n-butanol to exhaustion in foetidines 1 and 2. The n-butanol solution is concentrated and the residue is dried to obtain about 200 g of a butanol fraction which is fractionated as follows: 30 g of butanol fraction are chromatographed on 500 g of silica gel, eluting the column first with a 4:1 methylene chloride/methanol mixture, subsequently with a 7:3 mixture of the same solvents. The product contained in the fraction eluted with the 7:3 mixture is purified on a LiChroprep RP8 column, eluting with a methanol/water gradient. The fractions containing foetidines 1 and 2 are combined and concentrated to dryness under vacuum at a temperature below 30° C. and the residue is crystallized from acetone/hexane. 5.1 g of foetidine 1 are obtained, having the following characteristics: m.p. 157°–58° C.; $a_d$=−37.9 (c=0.31, MeOH).

$^1$H-NMR (300 MHz, DMSO $d_6$) 8.60 (1H, s, H-7), 8.19 (1H, t, J=5.2, H-10'), 8.15 (1H, d, J=8.6, H-12), 8.05 (1H, d, J=8.6, H-9), 8.04 (1H, t, J=5.2, H-19'), 7.80 (1H, t, J=7.8, H-11), 7.65 (1H, t, J=7.8, H-10), 7.35 (2H, d, J=8.6, H-3'+H-5'), 7.34 (2H, d, J=8.6, H-24'+H-28'), 7.29 (1H d, J=15.8, H-7'), 7.28 (1H, d, J=15.8, H-22'), 6.76 (4H, d, J=8.6 H-2'+H-6'+H-25'+H-27'), 6.36 (1H, d,J=15.8, H-8'), 6.35 (1H, d, J=15.8, H-21'), 5.58, 5.41 (2H, system AB, J=10.6, H-17), 5.18(2H, s, H-5), 3.21 (2H, m, H-11'), 3.13 (2H, m, H-18'), 2.84 (4H, bt, J=7.2, H-13'+H-15'), 2.02 (1H, m, H-19A), 1.96 (3H, s, CH$_3$CO), 1.90 (1H, m, H-19B), 1.74 (2H, m, H-12'), 1.55 (2H, m, H-16'), 1.46 (2H-17'), 0.84 (3H, t, J=7.2, H-18)

$^{13}$C-NMR (78.1 MHz, DMSO d6) δ: 175.23 (s, C-21), 170.81 (s, CH$_3$CO), 166.27 (s, C-9'), 165.83 (s, C-20'), 161.43 (s, C-16a), 159.40 (s, C-1'), 159.14 (s, C-15), 153.50 (s, C-2), 148.36 (s, C-13), 143.56 (s, C-3), 139.37 (d, C-7), 139.06 (d, C-22'), 131.74 (d, C-7), 130.58 (d, C-11), 130.33 (s, C-6), 129.63 (s, C-3'+C-5'), 129.56 (d, C-24'+C-28'), 129.40 (d, C-12), 128.83 (d, C-9), 128.23 (s, C-8), 127.78 (d, C-10), 126.23 (d, C-4'), 126.13 (s, C-23'), 123.42 (s, C-16), 119.01 (d, C-8'), 118.68 (d, C-21'),116.18 (d, C-2'+C-6'+C-25'+C-27'), 100.68 (d, C-14), 80.28 (d, C-20), 59.87 (t, C-17), 50.45 (t, C-5), 47.23 (t, C-13'), 45.36 (t, C-15'), 38.41 (t, C-18), 36.36 (t, C-11'), 33.40 (t, C-19), 26.99 (t, C-12'), 26.87 (t, C-17'), 24.04 (t, C-16'), 21.22 (q, CH$_3$CO), 9.29 (q, C-18).

From the crystallization mother liquors of foetidine 1, by purification in the same chromatographic eluent in reverse phase, foetidine 2 (1.2 g) is obtained, having the following characteristics:

m.p. 172°–4° C., α$_d$ −44.6 (c 0.35, MeOH). The NMR spectrum is superimposable to that of foetidine 1, except for the signal of —OCH$_3$ on the aromatic ring at 3.2 ppm.

EXAMPLE 2

Preparation of freeze-dried vials containing foetidine 1.

5 g of foetidine 1 are dissolved in 500 ml of distilled water containing 1.2 g of citric acid, the solution is filtered, sterilized and filled in sterile room into 100 vials which are quickly frozen and freeze-dried.

We claim:

1. A compound of formula I

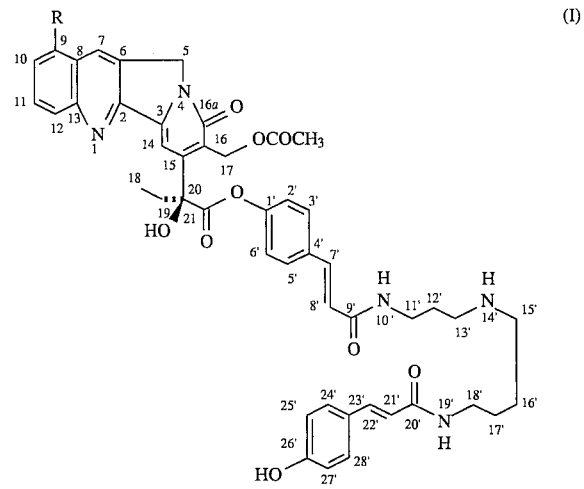

wherein R is hydrogen or methoxy.

2. The compound according to claim 1, which is foetidine 1 in which R is hydrogen.

3. The compound according to claim 1 which is foetidine 2 in which R is methoxy.

4. A pharmaceutical composition for the treatment of mammalian carcinoma or viruses in unit dosage form containing as the active ingredient 0.5 mg. to 200 mgs. per dose of a compound according to claim 1 and pharmaceutical excipients.

5. A pharmaceutical composition active against human carcinoma, containing a compound according to claim 4 in the dose of 50 mgs.

\* \* \* \* \*